(12) United States Patent
Foley et al.

(10) Patent No.: US 9,604,898 B2
(45) Date of Patent: *Mar. 28, 2017

(54) OZONOLYSIS OPERATIONS FOR GENERATION OF REDUCED AND/OR OXIDIZED PRODUCT STREAMS

(71) Applicant: P2 Science, Inc., New Haven, CT (US)

(72) Inventors: Patrick Foley, New Haven, CT (US); Yonghua Yang, New Haven, CT (US)

(73) Assignee: P2 Science, Inc., Woodbridge, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/415,327

(22) PCT Filed: Jul. 19, 2013

(86) PCT No.: PCT/US2013/051357
§ 371 (c)(1),
(2) Date: Jan. 16, 2015

(87) PCT Pub. No.: WO2014/015290
PCT Pub. Date: Jan. 23, 2014

(65) Prior Publication Data
US 2015/0183707 A1    Jul. 2, 2015

Related U.S. Application Data

(60) Provisional application No. 61/673,411, filed on Jul. 19, 2012, provisional application No. 61/784,376, filed on Mar. 14, 2013.

(51) Int. Cl.
| | | |
|---|---|---|
| $C07C\ 51/16$ | (2006.01) | |
| $C07C\ 51/373$ | (2006.01) | |
| $C07C\ 51/34$ | (2006.01) | |
| $C07C\ 45/40$ | (2006.01) | |

(52) U.S. Cl.
CPC ............ *C07C 51/373* (2013.01); *C07C 45/40* (2013.01); *C07C 51/34* (2013.01)

(58) Field of Classification Search
CPC ......... C07C 45/40; C07C 51/34; C07C 47/02; C07C 55/18; C07C 51/373
See application file for complete search history.

(56) References Cited

U.S. PATENT DOCUMENTS

| | | |
|---|---|---|
| 2,813,113 A | 11/1957 | Goebel et al. |
| 4,791,228 A | 12/1988 | Siclari et al. |
| 6,309,521 B1 | 10/2001 | Andrews et al. |
| 9,035,091 B2 * | 5/2015 | Foley ............... C07C 51/34 562/524 |
| 2007/0276165 A1 * | 11/2007 | Gutsche ............ C07B 41/08 568/959 |
| 2013/0177497 A1 | 7/2013 | Fitch et al. |

FOREIGN PATENT DOCUMENTS

WO    WO 02/48431 A2    6/2002

OTHER PUBLICATIONS

Maggiolo A. "Ozonization of Fatty Acids and Their Derivatives", *The Journal of the American Oil Chemists' Society*, (Apr. 1963), vol. 40, p. 161-164.

* cited by examiner

*Primary Examiner* — Yevegeny Valenrod
*Assistant Examiner* — Blaine G Doletski
(74) *Attorney, Agent, or Firm* — Cooley LLP; Ivor R. Elrifi; Heidi A. Erlacher

(57) ABSTRACT

The present invention relates to methods for safe and efficient use of hydrogen and oxygen in ozonolysis operations. The invention also relates to an ozonolysis process involving elements of both reductive and oxidative ozonolysis which are integrated in a continuous process. In one embodiment, the ozonolysis process of the present invention uses hydrogen and/or oxygen generated from water and electricity, which may be recycled to generate water and/or electricity.

2 Claims, 11 Drawing Sheets

OZONOLYSIS OPERATIONS FOR GENERATION OF REDUCED AND/OR OXIDIZED PRODUCT STREAMS

RELATED APPLICATIONS

This application is a national stage application, filed under 35 U.S.C. §371, of International Application No. PCT/US2013/051357, filed Jul. 19, 2013, which claims the benefit of and priority to U.S. Provisional Patent Application Nos. 61/673,411, filed Jul. 19, 2012 and 61/784,376, filed Mar. 14, 2013. The contents of each of these applications are hereby incorporated by reference in their entireties.

FIELD OF INVENTION

Embodiments disclosed herein are directed to an ozonolysis process involving an integrated process including both reductive and oxidative ozonolysis processes in a continuous process.

BACKGROUND

Ozonolysis is a highly atom-efficient oxidative transformation, with two of the three oxygen atoms from the ozone molecule being incorporated into the products. Due to its ease of generation and its efficiency with regard to the oxidative cleavage of olefins, ozone has found use in a wide variety of applications, including chemical manufacturing and water disinfection.

When used in chemical manufacturing, ozonolysis requires a second step that destroys the peroxide and/or ozonide present in the reaction mixture before products are isolated. In the case of oxidative ozonolysis, the peroxides are further heated and oxidized in the presence of oxygen ($O_2$) to generate products including carboxylic acid products. In the case of reductive ozonolysis, the peroxides and ozonides are quenched under reducing conditions, using hydrogen ($H_2$) to give carbonyls and/or alcohols as the major products.

All ozonolysis processes require electricity and oxygen in order to generate ozone, and in the case of reductive ozonolysis, hydrogen may be used, as well. Historically, industrial oxygen production has been carried out mainly through the distillation or zeolite treatment of air, while $H_2$ has been generated from the reformation of natural gas. See Cooke, S. J., *Industrial Gases, Kent and Riegel's Handbook of Industrial Chemistry and Biotechnology*, 11$^{th}$ ed., ch. 27, p. 1215 (2007); Hiller, H., *Gas Production: Introduction*, *Ullmann's Encyclopedia of Industrial Chemistry*, vol. 16, p. 403 (2012). More recently, however, electrolysis of water ($H_2O$) using proton exchange membranes (PEM) has become a common method of oxygen and hydrogen generation as well. In the electrolysis of water, 2 moles of hydrogen are produced for every mole of oxygen making it highly amenable to generation of starting materials for reductive ozonolysis processes, as both gases are required for such processes.

Regardless of source, oxygen must be treated with electricity to generate ozone for the ozonolysis process. The ozone is then carried to the ozone reactor as a 0.1-20% mixture in a stream of oxygen. During the ozonolysis reaction, only the ozone is consumed and thus the oxygen must then be discarded, recycled, or used for an alternative purpose. Due to the cost associated with oxygen production, the preferred option has been to recycle the oxygen for continued ozone generation, using a corona discharge technique. See Vezzù, G., et al. IEEE *Transactions on Plasma Science*, Vol. 37, No. 6, p. 890-896 (2009).

While this process can be relatively efficient, there is a hazard associated with explosion due to organic contamination of the oxygen stream that is being recycled. Multiple condensers, precipitators, and/or filters are thus employed to manage this risk.

In addition to hazard reduction, the cost of electricity in the generation of ozone is a significant expense, and therefore a clean and efficient source of electricity would be desirable for the ozone generation process. Both fuel cells and hydrogen burning gas turbines offer such a solution. Fuel cells and gas turbines can use hydrogen and oxygen to generate electricity, with the reaction products being water and heat. While oxygen from ambient air can be used for these fuel cells, the fuel cells run at optimum efficiency in the presence of high purity oxygen and hydrogen. See Buchi, F. N., et al. *On the Efficiency of Automotive $H_2/O_2$ PE Fuel Cell Systems*, 3$^{rd}$ European PEFC, Session B09 (Thursday, 7 Jul. 2005). The deficiencies in current ozonolysis processes are addressed by the current invention. The invention disclosed herein arranges the ozonolysis process in such a way that the excess oxygen and hydrogen that are generated from the electrolysis step can be used to efficiently run a fuel cell or a gas turbine, thus significantly offsetting the net electricity required to generate ozone in a single-pass system.

SUMMARY OF THE INVENTION

The present invention relates to performing ozonolysis for generating hydrogenated and/or oxidized ozonated products. In particular, the invention relates to an ozonolysis process for producing linear alkyl aldehydes (e.g., nonanal) and diacids (e.g., azelaic acid) or acid-esters (e.g., monomethyl azelate) by integrating both reductive and oxidative ozonolysis processes in a continuous process. The present invention also relates to methods of safe and/or efficient handling of gases, for example, hydrogen and oxygen. In one embodiment, electrolysis is used to generate gases for the ozonolysis process, thereby minimizing the need to recycle the oxygen through corona discharge. In one such embodiment, hydrogen and/or oxygen can or may be reclaimed via fuel cell or a turbine at the end of the ozonolysis process. In another embodiment, hydrogen and/or oxygen can or may be used in any other operations for which the gases are useful.

In one embodiment, the current invention provides an ozonolysis process, which uses oxygen and hydrogen from any source, where oxygen can be utilized as a reagent for generating ozone, and ozone can then be used in ozonolysis of fatty acid(s) and/or fatty acid ester(s) in an ozone reactor. In one embodiment, oxygen and/or hydrogen is generated by electrical means or by any other means of hydrolysis. In additional embodiments, oxygen and/or hydrogen is generated by any other means, including from distillation of air or from natural gas reformation.

In a process described herein, the fatty acid and/or fatty acid ester(s) can or may be inputted into the ozone reactor, where the fatty acid(s) and/or fatty acid ester(s) absorbs ozone to form an ozonated product stream. According to some elements of the current invention, the ozonated product stream include, without being limited to the listed examples, ozonides, peroxides, aldehydes, acids, esters, and any combination thereof. The ozonated product stream, according to the current invention can be used to generate hydrogenated products, for example, linear alkyl aldehydes (e.g., nonanal) and/or oxidized or oxygenated products, for example, diacids or acid-esters.

In one embodiment, without being limiting, the current invention provides an ozonolysis process which uses an ozone reactor. For example, the ozone reactor is a batch reactor, a continuous stirred-tank reactor, a loop reactor, a plug flow-type reactor, or a fixed bed-type reactor. In one embodiment, a batch reactor, a continuous stirred-tank reactor, or a loop reactor is used in the ozonolysis step. In one embodiment, a plug flow-type reactor or fixed bed-type reactor is used in the hydrogenation step.

According to the embodiments of the current invention, the ozonated product stream can or may be partially reduced in a hydrogenation chamber where hydrogenated products, for example, linear alkyl aldehydes are generated. In one embodiment, the mixture comprising aldehydes forms a biphasic layer as it leaves the hydrogenation chamber, one phase of which is an organic phase. The organic phase can then be fractionated by distillation or ion exchange into two or more fractions, one of which may comprise linear alkyl aldehydes (e.g., nonanal).

The organic phase fraction(s) not comprising linear alkyl aldehydes can or may then be oxidized in an oxidation chamber to generate oxidized products, for example, diacids or acid-esters. In one embodiment, this (e.g., "remaining") organic phase fraction comprises an oxo-acid or an oxo-ester, which is first distilled and then oxidized in an oxidation chamber. In one embodiment, the oxidation of distilled oxo-acid produces diacid.

In another embodiment, the organic phase fraction comprising an oxo-acid or oxo-ester is first oxidized in an oxidation chamber and then distilled, precipitated, and/or extracted to produce a diacid or esters such as an acid-ester and diester. In one embodiment, the diacid produced has a purity of at least 40%, 50%, 60%, 70%, 80%, 90%, 95%, or 99%.

The current invention provides that hydrogen gas can or may be streamed through a hydrogenation chamber for partial reduction of the ozonated product stream generated from reaction of fatty acid in an ozone reactor. In an embodiment, hydrogen is streamed continuously through the hydrogenation chamber.

In an embodiment, oxygen is streamed through the oxidation chamber to oxidize the remaining organic phase fraction (with or without further distillation) to produce diacids or acid-esters. Any unused or excess oxygen from ozone reactor, or oxidation chamber, or from both may be recycled as fuel for generation of ozone, water, or electricity, or any combination thereof.

In some embodiments of the current invention, any unused hydrogen from the hydrogenation chamber may be recycled, for example as fuel for generation of water or electricity, or both.

In an embodiment, the ozonolysis process may include a catalyst to facilitate oxidation of the ozonated product stream. In one embodiment, the catalyst may be a metal catalyst.

The invention provides that electricity may be generated in a device such as a fuel cell or a hydrogen burning gas turbine. The fuel cell, according to an embodiment, may be an alkaline fuel cell, a phosphoric acid fuel cell, or a proton exchange membrane (PEM) fuel cell.

In some embodiments, the current invention provides an electrolyzer for generating ozone, where the electrolyzer may be a PEM hydrolysis electrolyzer.

In another embodiment, the ozonolysis process of the current invention may include both oxidative and reductive processes. In some embodiments, oxygen and hydrogen used in ozonolysis process may be generated from water and electricity.

The current invention also provides an oxidative ozonolysis process, which may utilize oxygen as a reagent for generating ozone. The ozone generated may then be used to generate an ozonated product stream from fatty acid in an ozone reactor. The fatty acid may be inputted to the ozone reactor, where fatty acid may absorb ozone from the oxygen and/or ozone stream, and may form an ozonated product stream, which may include ozonides, peroxides, aldehydes, and acids and/or esters. The ozonated product stream may then be passed into an oxidation reactor, in which oxygen may be streamed continuously for oxidizing the ozonated product stream.

In an embodiment of the current invention, the streaming oxygen in the oxidation chamber may create an oxidative environment for a concurrent thermal scission of ozonides and for oxidation of the ozonated product (e.g., aldehydes).

The invention also provides that any remaining oxygen during generation of ozone and/or the oxidation of ozonated product stream may then be used to generate water and/or electricity. In certain embodiments, the invention provides that when oxygen is recycled to generate water and/or electricity, no oxygen may be recycled into the ozone reactor and substantially all or all of oxygen may be utilized in the ozonolysis process.

In another embodiment, any oxygen unused in the generation of ozone or oxidizing ozonated product stream or both in an oxidative ozonolysis process may be recycled to the ozone reactor after passing through distillation towers.

In the oxidative ozonolysis process of some embodiments of this invention, oxidation of the ozonated product stream includes a catalyst to facilitate oxidation. According to one embodiment of the current invention, a catalyst may be a metal catalyst.

In some embodiments, electricity for use in the oxidative ozonolysis may be generated using a device, for example, a fuel cell or a hydrogen burning gas turbine.

In an embodiment of the current invention, during oxidative ozonolysis, fatty acids may be introduced to the ozone reactor in a solvent selected from nonanoic acid, glycerol, water, and any combinations thereof.

An embodiment of the current invention provides that oxygen, hydrogen, and ozone may be generated in a single step. The oxygen used in generation of ozone may be recycled through an organic medium, wherein the organic medium is substantially purged of volatile components. In additional embodiments, the oxygen used for generating ozone or for oxidizing the ozonated product stream may be recycled after being passed through a chamber free of volatile, light organic materials or a chamber composed of only non-volatile, heavy organic materials.

In an embodiment, the current invention provides a reductive ozonolysis process integrated with the oxidative ozonolysis process, in which oxygen can or may be used as a reagent for generating ozone and the ozone can or may be used for generating an ozonated product stream from the fatty acid in an ozone reactor. In this embodiment, the fatty acid can or may be inputted in the ozone reactor, where the fatty acid can or may absorb ozone from the oxygen and/or ozone stream, and form an ozonated product stream. The ozonated product stream can or may then be transferred continuously to a hydrogenation chamber for hydrogenation, where a stream of hydrogen can or may reduce the ozonated product stream to produce aldehyde-rich products. The reduced ozonated product stream may then be distilled to produce aldehyde-rich products, such as linear alkyl aldehydes (e.g., nonanal), and for generation of diacids and/or acid esters.

In an embodiment of the reductive ozonolysis process, any hydrogen remaining unused in the reduction step is then used to generate water, electricity, or in any other operation that uses or requires hydrogen, such as down-stream processing, or other hydrogenation operations. The electricity, according to an embodiment of the reductive ozonolysis process of the current invention, can be generated in a source such as a fuel cell or hydrogen burning gas turbine.

The current invention also provides an ozonolysis process comprising reductive ozonolysis and oxidative ozonolysis. In one embodiment, the reductive ozonolysis occurs prior to the oxidative ozonolysis. In one embodiment, the process of the invention further comprises generating ozone prior to the reductive ozonolysis and the oxidative ozonolysis. In one embodiment, the ozone generated reacts with a fatty acid to produce an ozonated product.

In one embodiment, the process of the invention further comprises reacting a fatty acid with ozone prior to the reductive ozonolysis and the oxidative ozonolysis to produce an ozonated product. In one embodiment, the reaction between the fatty acid and the ozone comprises a solvent (e.g., nonanoic acid, glycerol, and water, or a combination thereof).

In one embodiment, the ozonated product comprises an ozonide, peroxide, aldehyde, or acid.

In one embodiment, the ozonated product is reduced in a reductive ozonolysis process. In one embodiment, the reduced product comprises an aldehyde. In one embodiment, the reductive ozonolysis comprises a catalyst (e.g., a metal catalyst). In one embodiment, the reductive ozonolysis comprises hydrogen gas. In a further embodiment, any unused hydrogen gas is recycled.

In one embodiment, the reduced product forms biphasic liquid layers. In one embodiment, the process of the invention further comprises separating the organic phase of the biphasic liquid layers. In another embodiment, the process of the invention further comprises purifying (e.g., distilling, and ion-exchanging) the organic phase to obtain an aldehyde. In one embodiment, the aldehyde is a linear aldehyde.

In one embodiment, the ozonated product is oxidized in an oxidative ozonolysis process. In one embodiment, the oxidized product comprises a diacid. In one embodiment, the oxidative ozonolysis process comprises a catalyst (e.g., a metal catalyst). In one embodiment, the oxidative ozonolysis process comprises oxygen. In a further embodiment, any unused oxygen is recycled.

The current invention also provides an ozonolysis process comprising: 1) reacting a fatty acid with ozone to produce an ozonated product; 2) reducing the ozonated product under reductive ozonolysis to produce a reduced product; 3) separating an aldehyde from the reduced product; 4) oxidizing the reduced product to produce an oxidized product; and 5) separating a diacid or acid ester from the oxidized product. In one embodiment, the process of the invention further comprises generating ozone prior to step 1). In one embodiment, step 2) comprises hydrogen gas. In a further embodiment, any unused hydrogen gas is recycled. In another embodiment, step 4) comprises oxygen. In a further embodiment, any unused oxygen is recycled.

The invention also provides partially reduced products and/or oxygenated products prepared by the hybrid ozonolysis process described herein. In one embodiment, the products produced by the methods of the invention are linear aldehyde, oxo-acid, oxo-ester, acid-ester, and/or diacid.

Unless otherwise defined, all technical and scientific terms used herein have the meaning as commonly understood by one of ordinary skill in the art to which this invention pertains. In the specification, the single forms also include the plural unless the context clearly dictates otherwise. Although methods and materials similar or equivalent to those described herein can be used in the practice or testing of the present invention, suitable methods and materials are described below. In addition, the materials, methods, and examples are illustrative only and are not intended to be limiting.

Other features and advantages of the invention will be apparent from the detailed description and claims.

In order to understand the invention and to demonstrate how it may be carried out in practice, embodiments are now described, by way of non-limiting examples, with reference to the accompanying drawings.

DETAILED DESCRIPTION OF THE INVENTION

Figure 1:
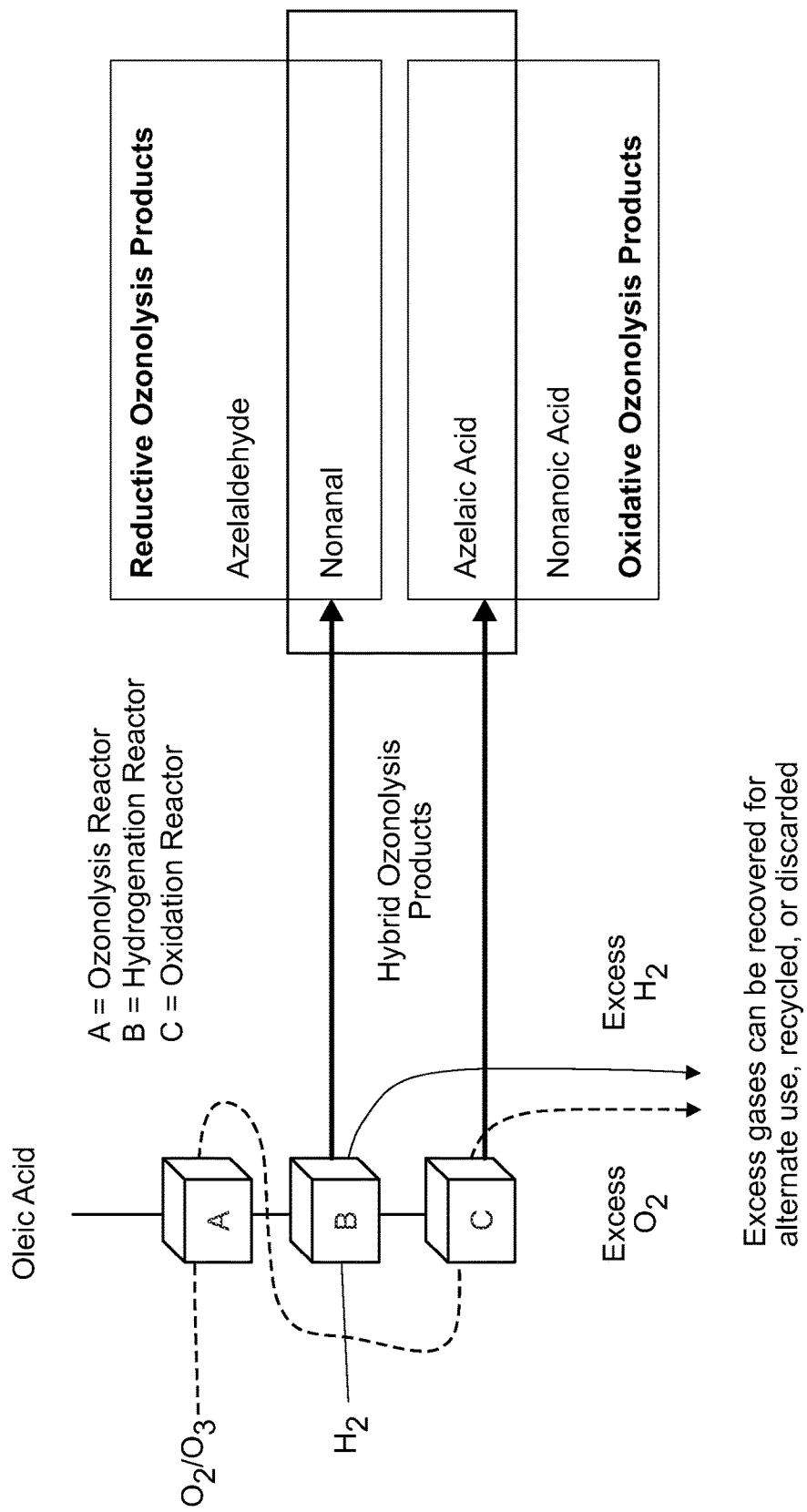
FIG. 1 shows a representative schematic of hybrid ozonolysis of oleic acid to generate diacids and linear alkyl aldehydes. Oleic acid is used only as an example.

The materials, articles, and methods described herein may be understood more readily by reference to the following detailed description of specific aspects of the disclosed subject matter and the Examples included therein. Before the present materials, articles, devices, and methods are disclosed and described, it is to be understood that the aspects described below are not limited to specific methods or specific reagents, and as such may vary. It is also to be understood that the terminology used herein is for the purpose of describing particular aspects only and is not intended to be limiting.

Also, throughout this specification, various publications including patent documents and scientific articles are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

The following paragraphs describe the invention, but only as an example and in no way limited solely to what is expressly disclosed. Any inherent or well established method in the art, which may be in use at the time of invention of the current embodiments and/or any improvements thereof, are inherently incorporated herein.

Hybrid Ozonolysis

Unlike the processes disclosed in the art, this invention describes an ozonolysis process specifically for producing linear alkyl aldehydes (e.g., nonanal) and diacids (e.g., azelaic acid) or acid-esters (e.g., monomethyl azelate) by integrating both reductive and oxidative ozonolysis processes in a continuous process. The ozonolysis process of the current invention is referred to as a hybrid ozonolysis process.

The hybrid ozonolysis process described herein may be used to generate both diacids (and/or acid-esters) and linear alkyl aldehydes from the ozonolysis of unsaturated fatty acids and/or fatty acid esters.

In contrast, previous ozonolysis processes have been limited to product sets that result in either acid and/or ester products (i.e., oxidative ozonolysis), or aldehyde and/or alcohol products (i.e., reductive ozonolysis). For example, oxidative ozonolysis processes were described in U.S. Pat. No. 2,813,113 and US Patent Application 2012/0245375, and the reductive ozonolysis of fatty acids in aqueous conditions was described in U.S. Pat. No. 3,504,038. Other related processes have been described in 1) US 2005/0010069 A1, which uses alcoholic processing conditions to form resins; 2) WO 2010/078498 A1, which uses alcohols such as glycerol in the process to generate polyols for resins; 3) WO 2012/168770 A1, which uses ozone to make formulations of medicinal interest; 4) WO 2010/011134 and U.S. Pat. No. 7,825,277 which describe general ozonolysis using microreactors; and 5) U.S. Pat. No. 5,543,565, which describes a method for enhancing azelaldehyde oxidation using a fritted tube.

In one embodiment of the invention, the purity of the linear aldehyde, oxo-acid, oxo-ester, acid-ester, and/or diacid produced by the methods described herein is more than about 45%. In one embodiment, the purity of the linear aldehyde, oxo-acid oxo-ester, acid-ester, and/or diacid produced by the methods of the present invention is more than about 60%. In one embodiment, the purity of the linear aldehyde, oxo-acid, oxo-ester, acid-ester, and/or diacid produced by the methods of the present invention is more than about 70%. In one embodiment, the purity of the linear aldehyde, oxo-acid, oxo-ester, acid-ester, and/or diacid produced by the methods of the present invention is more than about 80%. In one embodiment, the purity of the linear aldehyde, oxo-acid, oxo-ester, acid-ester, and/or diacid produced by the methods of the present invention is more than about 90%. In one embodiment, the purity of the linear aldehyde, oxo-acid, oxo-ester, acid-ester, and/or diacid produced by the methods of the present invention is more than about 95%. In one embodiment, the purity of the linear aldehyde, oxo-acid, oxo-ester, acid-ester, and/or diacid produced by the methods of the present invention is more than about 99%.

The hybrid ozonolysis process of the current invention involves both reduction and oxidation steps of fatty acid(s) and/or fatty acid ester(s), which are carried out in the same integrative process to obtain aldehydes and/or alcohols, as well as acids and esters. See FIG. 1. In this method a fatty acid and/or fatty acid ester may be inputted in a solvent selected from nonanoic acid, glycerol, water, and any combination thereof, where the fatty acid and/or fatty acid ester absorbs ozone from the oxygen and/or ozone stream in an ozone reactor, thereby forming a mixture of ozonated products or product stream, for example, ozonides, peroxides, acids, esters and/or aldehydes. Hydrogen can then be streamed through a hydrogenation chamber for partial reduction of the ozonated product stream formed in the ozone reactor to produce an aldehyde mixture. One fraction of the aldehyde mixture produced in the hydrogenation chamber may be distilled off, and a second fraction (e.g., "remaining fraction") of the aldehyde mixture may then be oxidized in an oxidation chamber with oxygen to produce acids. The "hybrid ozonolysis" approach may be used to generate optimal products through ozonolysis of fatty acid(s) and/or fatty acid ester(s), for example, linear alkyl aldehydes and diacids and esters (i.e., acid-ester or diester).

The hybrid ozonolysis process may be especially beneficial when converting oils and fatty acid mixtures that have high monounsaturated fatty acid content. These mixtures may include high oleic safflower, sunflower, and canola oils, as well as tailored algae oils with controlled chain lengths, saturation levels and functional group additions. The monounsaturation may occur at a variety of positions in the fatty acid chain to give preferred mixtures of diacid and linear aldehyde. The diacids and acid-esters may for example be used in polymers, lubricants, cosmetics, pharmaceuticals, and agrochemicals and the like. The linear alkyl aldehydes may for example be used directly in flavors and fragrances, or as precursors to flavors and fragrances, Guerbet alcohols, plasticizers, surfactants, and various other specialty chemicals, and the like.

The current invention provides an ozonolysis process, which may use oxygen and hydrogen, where oxygen may be utilized as a reagent for generating ozone, and ozone may then be used in ozonolysis of fatty acid in an ozone reactor. The ozonolysis process of the current invention may use oxygen and hydrogen generated from water either by electrical means or by any other means of hydrolysis, or oxygen and hydrogen generated by any other means, as well, including from the distillation of air or from natural gas reformation. The fatty acid may be inputted into the ozone reactor, where it absorbs the ozone, to form an ozonated product stream. According to some elements of the current invention, the ozonated product stream may include, without being limiting, peroxides, aldehydes, acids, esters, and any combination thereof. The ozonated product stream, according to the current invention is used to generate linear alkyl aldehydes (e.g., nonanal) and diacids.

According to the embodiments of the current invention the ozonated product stream may be partially reduced in a hydrogenation chamber where aldehydes are generated. The mixture comprising aldehydes may form a biphasic layer while leaving the hydrogenation chamber one phase of which is an organic phase. The organic phase may then be fractionated to two or more fractions. One of the fractions, according to some embodiments of the current invention, may contain linear alkyl aldehyde, for example (without limiting to the examples herein) hexanal, heptanal, octanal, nonanal, decanal, undecanal, dodecanal, or tridecanal. Another organic phase fraction may contain an oxo-acid and or/ester, for example (without limiting to the examples herein) 12-oxododecanoic acid, 11-oxoundecanoic acid, 10-oxodecanoic acid, 9-oxononanoic acid, 8-oxooctanoic acid, 7-oxoheptanoicacid, or 6-oxohexanoic acid or their corresponding esters. In one embodiment of hybrid ozonolysis described herein, the fraction containing the oxo-acid is carried onto oxidation to form a diacid.

Accordingly, the present invention also relates to the partially reduced products produced by the hybrid ozonolysis process described herein. In one embodiment, the invention relates to oxo-acid or oxo-ester produced by a method that includes (a) providing oxygen and hydrogen, wherein said oxygen is utilized as a reagent for generating ozone; wherein said ozone is used in ozonolysis of a fatty acid or fatty acid ester in an ozone reactor; (b) inputting said fatty acid or fatty acid ester into said ozone reactor, in which said fatty acid or fatty acid ester absorbs said ozone, thereby forming a mixture comprising ozonated product stream comprising one or more compounds selected from ozonides, peroxides, aldehydes, esters, and acids; and (c) generating a plurality of partially reduced products comprising linear alkyl aldehydes and said oxo-acid or oxo-ester by: (i) partially reducing said ozonated product stream after said ozonated product stream enters a hydrogenation chamber to generate said plurality of partially reduced products comprising largely aldehydes, wherein said aldehydes, when in the presence of water, form two layers comprising an organic phase while leaving the hydrogenation chamber; (ii) fractionating said organic phase to separate linear alkyl aldehydes from the remaining organic phase which comprises said oxo-acid or oxo-ester; and (iii) separating said oxo-acid or oxo-ester from the remaining organic phase after fractionation at step (ii); thereby generating said oxo-acid or oxo-ester in pure form. In some embodiments, the separation at step (iii) is performed by distillation. In some embodiment, at least a portion of the separated oxo-acid or oxo-ester is delivered to an oxidation chamber, resulting in the generation of oxygenated products comprising a diacid or acid-ester. In other embodiments, the separated oxo-acid or oxo-ester is not subject to oxidation to generate a diacid or acid-ester.

In an embodiment, the mixture leaving the hydrogenation chamber is biphasic in the presence of water, where a coalescer and/or phase separator can or may be used to separate the organic phase from the aqueous phase. The coalescer, according to the current invention can be, without being limited to the examples herein, PALL'S PHASESEP® A/S Series Liquid/Liquid Coalescer, PALL'S PHASESEP® Coalescer, or PALL'S PHASESEP® FR1 Series Liquid/Liquid Coalescer. The phase separator, according to the current invention can be, without being limited to the example herein, a centrifuge such as Rousselet Robatel Centrifugal liquid/liquid separators.

In one embodiment, the organic phase fraction comprises an oxo-acid or oxo-ester, which is first distilled and then oxidized in an oxidation chamber. The oxidation of distilled oxo-acid or oxo-ester produces diacid or acid-ester.

In another embodiment, the organic phase fraction comprising oxo-acid or oxo-ester leaving the hydrogenation chamber is first oxidized in an oxidation chamber and then further distilled, precipitated, and/or extracted to produce pure diacid or acid-ester.

According to the current invention, diacid or acid-ester may be produced in one of two ways. In one embodiment oxo-acid or oxo-ester may be distilled out from the product mixture and then "pure" oxo-acid or oxo-ester may be oxidized to get pure diacid or acid-ester. In another embodiment, oxo-acid or oxo-ester may be oxidized in the "impure" product stream, and then the diacid or acid-ester may be separated afterwards by distillation, precipitation and/or extraction.

A catalyst may be used to facilitate oxidation in the oxidation reactor and/or hydrogenation in the hydrogenation reactor, when the mixture of ozonides, peroxides, acids, esters and/or aldehydes may be transferred continuously through the reactor(s). In one embodiment, the catalyst is a metal catalyst. The catalyst can be any metal, for example, without being limiting, Mn (Manganese). Other catalysts suitable for the methods of the current invention are: Pt (Platinum), Pd (Palladium), Ni (Nickel), Ru (Ruthenium), and other commercially available catalysts suitable for use in ozonolysis.

In an embodiment of the current invention, the oxo-acid or oxo-ester in one of the fractions during ozonolysis is then be oxidized to its corresponding diacid or acid-ester in the presence of oxygen gas and an optional catalyst that includes, without being limited to the examples herein, Mn (Manganese), Os (Osmium), Pt (Platinum), Pd (Palladium), Cu (Copper), or Ru (Ruthenium), any commercially available catalyst suitable for use in oxidation, or any combination thereof.

Ozonolysis of olefins can or may be performed at moderate to elevated temperatures whereby the initially formed molozonide rearranges to the ozonide, which can or may then be converted to a variety of products. Although not wishing to be bound by theory, it is presently believed that the mechanism of this rearrangement involves dissociation into an aldehyde and an unstable carbonyl oxide, which recombine to form the ozonide.

In one embodiment, hybrid ozonolysis of a fatty acid is performed to generate an acid and/or an aldehyde. In one embodiment, fatty acid is passed through an ozone reactor as a thoroughly mixed emulsion in water. In one embodiment, if the mixture leaving the hydrogenation chamber is biphasic in the presence of water, a coalescer and/or phase separator is used to separate the desired organic phase from the aqueous layer. In one embodiment, the organic phase is fractionated by distillation or ion exchange to give a fraction containing an aldehyde. In one embodiment, the remaining organic phase after fractionation is oxidized after entering into an oxidation chamber, resulting in the generation of oxygenated products comprising diacids and/or acid-esters. In one embodiment, the balance of the organic mixture is further distilled to generate a high purity fraction of an oxo-acid or oxo-ester. In one embodiment, the oxo-acid is oxidized in an oxidation chamber. For example, oxo-acid or oxo-ester is taken on wholly to be oxidized in an oxidation chamber with diacid or acid-ester being recovered in high purity after oxidation by distillation, precipitation, and/or extraction. In one embodiment, excess oxygen and/or hydrogen may be recovered for alternate use, recycled, or discarded.

In one embodiment, hybrid ozonolysis is performed on a fatty acid and the ozonated product stream is then partially hydrogenated to produce an aldehyde in a hydrogenation reactor. In one embodiment, the aldehyde is distilled off in a distiller or a distillation tower. In one embodiment, the remaining ozonated product stream is oxidized in an oxidation chamber to generate acids. In one embodiment, excess oxygen and excess hydrogen are fed into a fuel cell to generate electricity and/or water. For example, excess oxygen may be recycled to the ozone reactor.

The current invention also provides an ozonolysis process comprising reductive ozonolysis and oxidative ozonolysis. In one embodiment, the reductive ozonolysis occurs prior to the oxidative ozonolysis. In one embodiment, the process of the invention further comprises generating ozone prior to the reductive ozonolysis and the oxidative ozonolysis. In one embodiment, the ozone generated reacts with a fatty acid to produce an ozonated product.

Ozone used in the process of the invention may be generated by any method known in the art. For example, ozone may be generated by the various methods described herein.

In one embodiment, the process of the invention further comprises reacting a fatty acid with ozone prior to the reductive ozonolysis and the oxidative ozonolysis to produce an ozonated product. In one embodiment, the reaction between the fatty acid and the ozone comprises a solvent (e.g., nonanoic acid, glycerol, and water, and a combination thereof).

A fatty acid is a carboxylic acid with long aliphatic hydrocarbon chains. The aliphatic hydrocarbon chains may be either saturated or unsaturated and may contain from at least 3 carbon atoms. For example, the aliphatic hydrocarbon chains may contain 3, 4, 5, 6, 7, 8, 9, 10, 11, 12, 13, 14, 15, 16, 17, 18, 19, 20, 21, 22, 23, 24, 25, 26, 27, 28, 29, 30, or more carbon atoms.

The solvent for the reaction between the fatty acid and the ozone can be any solvent suitable for carrying out the reaction. For example, the solvent may be aqueous or non-aqueous. For example, the solvent may be an acid or an alcohol. For example, the acid may be a carboxylic acid (e.g., RC(O)OH). For example, the carboxylic acid is nonanoic acid. For example, the alcohol is a polyol (i.e., a compound having more than one hydroxyl groups). For example, the polyol is glycerol. For example, the solvent may be water.

In one embodiment, the ozonated product comprises an ozonide, peroxide, aldehyde, or acids (e.g., carboxylic acids). In a further embodiment, the ozonated product may comprise additional products, such as esters.

In one embodiment, the ozonated product is reduced in a reductive ozonolysis process. In one embodiment the reduced product comprises an aldehyde. In one embodiment, the reductive ozonolysis process comprises a catalyst (e.g., a metal catalyst). In one embodiment, the reductive ozonolysis process comprises hydrogen gas. In a further embodiment, any unused hydrogen gas is recycled.

The catalyst can be any catalyst suitable for conducting reductive ozonolysis known in the art. For example, the catalyst is selected from the catalyst described herein.

The hydrogen gas that is not consumed in the reductive ozonolysis process may be recycled and/or reused. For example, the unused hydrogen gas may be used for generation of water or electricity, or both, as described herein.

In one embodiment, the reduced product forms biphasic liquid layers. In one embodiment, the process of the invention further comprises separating the organic phase of the biphasic liquid layers. In another embodiment, the process of the invention further comprises purifying (e.g., distilling, and ion-exchanging) the organic phase to obtain an aldehyde. In one embodiment, the aldehyde is a linear aldehyde.

The product after the reductive ozonolysis comprises aldehyde (e.g., alkyl aldehyde). For example, the alkyl aldehyde is a linear alkyl aldehyde (e.g., nonanal). For example, the aldehyde is at least 40%, 50%, 60%, 70%, 80%, 90%, 95%, or 95% pure. The product after the reductive ozonolysis may also comprise oxo-acid or oxo-ester. For example, the oxo-acid or oxo-ester is 9-oxononanoic acid or 9-oxo nonanoate methyl ester). For example, the oxo-acid or oxo-ester is at least 40%, 50%, 60%, 70%, 80%, 90%, 95%, or 95% pure.

In one embodiment, the ozonated product is oxidized in an oxidative ozonolysis process. In one embodiment, the oxidized product comprises a diacid or acid-ester. In one embodiment, the oxidative ozonolysis comprises a catalyst (e.g., a metal catalyst). In one embodiment, the oxidative ozonolysis comprises oxygen. In a further embodiment, any unused oxygen is recycled.

In one embodiment, the ozonated product undergoes oxidative ozonolysis after the reductive ozonolysis of the ozonated product is performed. For example, the organic phase of the biphasic liquid layers formed by the reduced product undergoes oxidative ozonolysis.

The catalyst can be any catalyst suitable for conducting oxidative ozonolysis known in the art. For example, the catalyst is selected from the catalyst described herein.

The product after the oxidative ozonolysis comprises diacid and/or acid-ester. For example, the diacid or acid-ester is azelaic acid or monomethyl azelate. For example, the diacid is at least 40%, 50%, 60%, 70%, 80%, 90%, 95%, or 95% pure.

The oxygen that is not consumed in the oxidative ozonolysis may be recycled and/or reused. For example, the unused oxygen may be used for generation of water, ozone, or electricity, or a combination thereof, as described herein.

The current invention also provides an ozonolysis process comprising: 1) reacting a fatty acid with ozone to produce an ozonated product; 2) reducing the ozonated product under reductive ozonolysis to produce a reduced product; 3) separating an aldehyde from the reduced product; 4) oxidizing the reduced product to produce an oxidized product; and 5) separating a diacid from the oxidized product. In one embodiment, the process of the invention further comprises generating ozone prior to step 1). In one embodiment, step 2) comprises hydrogen gas. In a further embodiment, any unused hydrogen gas is recycled. In another embodiment, step 4) comprises oxygen. In a further embodiment, any unused oxygen is recycled.

An example of the hybrid ozonolysis of the current invention, without being limited to the example herein, is shown in FIG. 1. As shown in the scheme in FIG. 1, ω-9 oleic acid may be passed through a reactor (A) where gaseous ozone and oxygen may be introduced for reaction with ω-9 oleic acid. The oleic acid may react with ozone at the sites of unsaturation on the fatty acid, and may form a mixture of ozonides, peroxides, and aldehydes, as well as small amounts of acids and/or esters as byproducts. The ozonized oleic mixture may then be passed into a hydrogenation chamber (B) where peroxides and ozonides may be reduced in the presence of hydrogen and a suitable catalyst. Examples of such catalysts include, without being limited to those disclosed herein, Pd or Pt. The hydrogenation process may produce a solution of largely aldehyde products, with small amounts of carboxylic acid and/or ester byproducts. In an embodiment, more than about 70% aldehydes are produced, and less than about 30% of carboxylic acid and/or ester are produced. In another embodiment, more than about 80% aldehydes and less than about 20% of acids and/or ester are produced. In another embodiment, more than about 90% aldehydes and less than about 10% of acids and/or ester are produced.

In an embodiment of the current invention fatty acid (or ω-9 oleic acid, as shown in FIG. 1) may be passed through an ozone reactor as a thoroughly mixed emulsion in water. In an embodiment, the entire emulsion may pass through the ozonolysis reactor and the hydrogenation reactor.

The organic phase may then be fractionated, preferably by distillation, but optionally by ion exchange or any other mean, to give a fraction containing the desired linear alkyl aldehyde, e.g., nonanal in FIG. 1. The balance of the organic mixture may then be further distilled to generate a high purity fraction of acid (e.g., 9-oxononanoic acid), which may then be oxidized in an oxidation chamber (C), as shown in FIG. 1. The high purity fraction may also be oxidized in an oxidation chamber (C), with diacid being recovered in high purity after oxidation by distillation, precipitation, and/or extraction.

In one embodiment the purity of 9-oxononanoic acid may be more than about 45%. In one embodiment the purity of 9-oxononanoic acid may be more than about 60%.

The ozone for embodiments of the current invention may be generated from oxygen using any commercial or non-commercial technology, including a corona discharge apparatus, a water electrolyzer, or from a combination of a water electrolyzer and a corona discharge apparatus. The oxygen used for the ozone generation may be from any reasonable source, including air, distilled air, and/or, from the electrolysis of water. The hydrogen for this process may be generated by any conventional commercial means, including the reformation of natural gas, or, preferably, from the electrolysis of water. Gases may be introduced to the process but may not fully be consumed and may then be recovered and used for an alternative purpose, recycled into the process, or discarded. The oxygen that may be present in the ozone reactor may be carried on for use in the oxidation reactor, or different sources of oxygen may be used.

In one embodiment of the current invention, any unused or excess hydrogen from the hydrogenation chamber during hybrid ozonolysis may be used to generate water and/or electricity.

In another embodiment, any excess oxygen in the oxidation chamber may also be used to generate water and/or electricity, where no oxygen may be recycled into the ozone reactor and substantially all of the oxygen may be utilized. Alternatively, unused oxygen from the oxidation chamber may be recycled to the ozone reactor after passing through distillation towers.

In some embodiments of the current invention, a fuel cell or a gas turbine may be used to generate electricity, which may then be used for electrolytic production of oxygen and hydrogen for use in the ozonolysis process.

The ozonolysis process may be carried out in a continuous fashion, where fatty acid may be fed into the beginning of the process at a continuous rate over multiple hours and similarly being passed from the initial reactor into subsequent downstream processes at a corresponding continuous rate over multiple hours. In one embodiment, the fatty acid and gas in-put flow, and gas and ozonolysis product out-put flow to and from chambers may be continuous without interruption. In another embodiment, the flow may be with interruption, where the interruption may be a single interruption or multiple interruptions. The single or multiple interruptions, according to some embodiments may be scheduled or random.

General Methods of Ozonolysis

The ozonolysis in the current invention may be carried out under virtually atmospheric pressure conditions. In this context, virtually atmospheric pressure conditions are understood as meaning pressures of 1 to about 3 bar, or as is customary in industry in order to prevent infiltration of air into hydrogenation reactor. The reduction of the ozonolysis products may be carried out under the virtual atmospheric condition. In another embodiment, hydrogenation may be carried out under pressure of up to 50 bar, thereby increasing the rate of hydrogenation.

In one embodiment, the ozonolysis process of the current invention may not require any pressure and may not involve an increase in the rate of hydrogenation.

The formation of the ozonides and oxidation to form two carboxylic acid groups may be applicable to compounds containing carbon-carbon double bonds. In one embodiment, the process can be useful for forming carboxyl groups in compounds containing from about 8 to about 30 carbon atoms and one or more double bonds. Fatty acids such as carboxylic acids, their nitriles, amides, esters and the like or alkene compounds can or may be used as feed for the process.

The ozonolysis process of the current invention may be incorporated into other ozonolysis-based chemical manufacturing technologies. Technologies where the ozonolysis of the current invention may be included, without being limited to the examples, include the ozonolysis of oleochemicals such as a fatty acid or stereoisomer or ester thereof, a wax ester, or a long-chain alkenone. For example, the aliphatic compound is selected from oleic acid, linoleic acid, linolenic acid, gadoleic acid, erucic acid, palmitoleic acid, myristoleic acid, petroselenic acid, vaccenic acid, ricinoleic acid, sappienic acid, stereoisomers thereof, and esters thereof.

The methods of the current invention may be used to or incorporated into a system to produce a large variety of products based on fats or oils for various uses, such as specialties for polymer applications, biodegradable mineral oil replacements for lubricants, and surfactants and emulsifiers for home and personal-care industries. For example, ozonolysis of oleic acid may produce azelaic acid, which then may be used in producing polyamides (e.g., nylon 6.9, nylon 6.6.9) or polyurethanes (e.g., laminating adhesives).

An ozone reactor, according to the current invention, may be any commercially available reactor suitable for incorporation in the method of the current invention. For example, an OCUBE® (Thales Nano, Inc.) ozonolysis system may be incorporated and/or modified as needed for use in the current invention. The OCUBE® works by continuous-flow of fatty acid, which may be combined with ozone, generated from an in-built ozone reactor, at temperatures between room temperature and −25° C. The ozonide formed may then be immediately mixed with an oxidative or reductive quench reagent, under cooling, to generate the required product. The product elutes from the reactor in minutes (e.g., for quick analysis). The ozone production may be turned off, so that other low temperature reactions may be performed. The ozonolysis of the current invention may be scaled for large scale industrial production with batch size from about 20 to about 500 kg.

A fuel cell, according to the current invention, may be a device that converts the chemical energy from a fuel into electricity through a chemical reaction with oxygen or another oxidizing agent. Hydrogen may be a fuel, but hydrocarbons such as natural gas and alcohols like methanol may be used. Fuel cells of the current invention are different from batteries in that they may require a constant source of fuel and oxygen to run, but may produce electricity continually for as long as these inputs are supplied.

Many types of fuel cells are contemplated for use in this invention. Fuel cells will consist of an anode (negative side), a cathode (positive side) and an electrolyte that allows charges to move between the two sides of the fuel cell. Electrons are drawn from the anode to the cathode through an external circuit, producing direct current electricity. As the main difference among fuel cell types is the electrolyte, fuel cells may be classified by the type of electrolyte they use. Fuel cells may come in a variety of sizes. Individual fuel cells may produce very small amounts of electricity; about 0.7 volts, so cells are "stacked," or placed in series or parallel circuits, to increase the voltage and current output to meet an application's power generation requirements. In addition to electricity, fuel cells may produce water, heat and, depending on the fuel source, very small amounts of nitrogen dioxide and other emissions. The energy efficiency of a fuel cell may be between 40-60%, up to 85%, or higher if waste heat is captured for use, and if the hydrogen and oxygen are recycled, as in the current invention.

The current invention may involve a gas turbine for generation of electricity. A gas turbine, also known as a combustion turbine, is a type of internal combustion engine. The turbine may have an upstream rotating compressor coupled to a downstream turbine, and a combustion chamber in-between. Energy may be added to the gas stream in the combustor, where fuel may be mixed with air and ignited. In the high pressure environment of the combustor, combustion of the fuel may increase the temperature. The products of the combustion may be forced into the turbine section. In the turbine section, the high velocity and volume of the gas flow may be directed through a nozzle over the turbine's blades, spinning the turbine which powers the compressor and, for some turbines, drives their mechanical output. The energy given up to the turbine comes from the reduction in the temperature and pressure of the exhaust gas. Various types of gas turbines may be used in the current invention, including aeroderivative gas turbines, auxiliary power units (APU), industrial gas turbines for power generation, compressed air energy storage, microturbines, miniature gas turbines, and other similar turbines suitable for use in an ozonolysis process, as in the current invention.

General Definitions

In this specification and in the claims that follow, reference is made to a number of terms, which shall be defined to have the following meanings: All temperatures are in degrees Celsius (° C.) unless otherwise specified.

The following examples are illustrative, but not limiting, of the methods, articles, and materials of the present invention. Other suitable modifications and adaptations of the variety of conditions and parameters normally encountered in the disclosed method and that are obvious to those skilled in the art are within the spirit and scope of the embodiments.

As used herein, the singular forms "a," "an," and "the" include plural referents unless the context clearly dictates otherwise. Thus, for example, reference to "a fatty acid" includes not only a single fatty acid but also a combination or mixture of two or more different fatty acids, reference to "a derivative" includes a single derivative as well as two or more derivatives, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the terms "ozonated product stream" and "ozonated products" are used interchangeably, and may refer to either singular or plural depending on the context.

EXAMPLES

Example 1

Hybrid Ozonolysis

Hybrid ozonolysis of oleic acid, for example, is performed to generate azelaic acid and nonanal. A representative product flow of hybrid ozonolysis of oleic acid is shown in FIG. 1. ω-9 oleic acid, as shown in FIG. 1, is passed through an ozone reactor as a thoroughly mixed emulsion in water. If the mixture leaving the hydrogenation chamber is biphasic in the presence of water, a coalescer and/or phase separator is used to separate the desired organic phase from the aqueous layer. The organic phase is then fractionated by distillation or by ion exchange, to give a fraction containing the desired linear alkyl aldehyde, nonanal. The balance of the organic mixture is then further distilled to generate a high purity fraction of 9-oxononanoic acid, which is then oxidized in an oxidation chamber (C), or is taken on wholly to be oxidized in an oxidation chamber (C), with diacid being recovered in high purity after oxidation by distillation, precipitation, and/or extraction. Excess oxygen and/or hydrogen may be recovered for alternate use, recycled, or discarded. See FIG. 1.

Example 2

Hybrid Ozonolysis—Recycling Hydrogen and Oxygen

Figure 2:
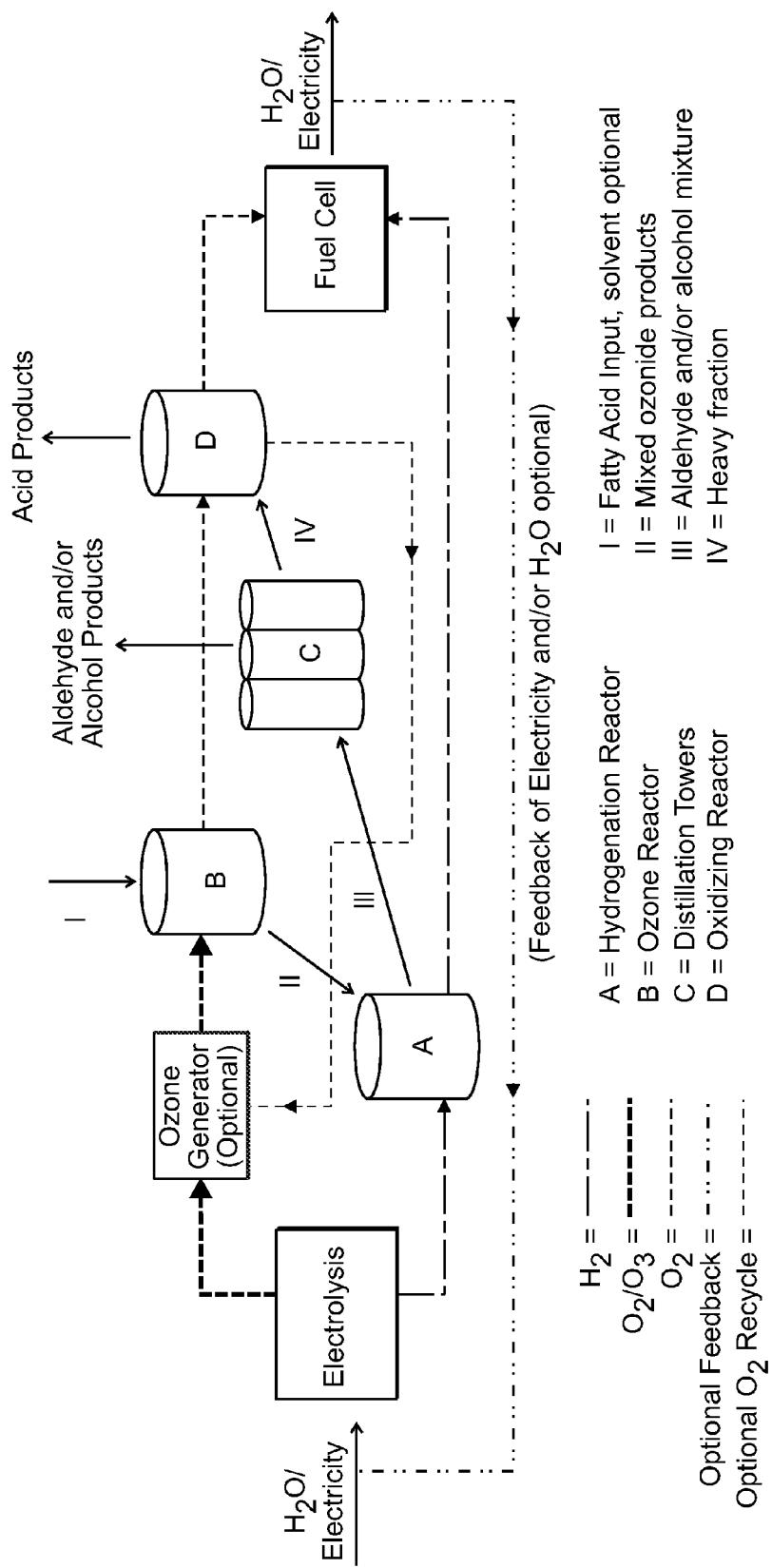
FIG. 2 shows representative schematic of gas flow through a hybrid of the reductive and oxidative ozonolysis processes, where the unbroken lines marked with I-IV and the unbroken lines with arrows directing away from chambers C and D represent the flow of organic reactants and products.

A hybrid ozonolysis may be performed following the schematic in FIG. 2. In the schematic in FIG. 2 of gas flow through a hybrid of the reductive and oxidative ozonolysis processes, the unbroken lines marked with I-IV and the unbroken lines with arrows directing away from chambers C and D represent the flow of organic reactants and products. In this method, fatty acid is added to an ozone reactor (B), where ozonolysis of oleic acid or any vegetable oil fatty acid (as an example only) can be initiated. The ozonated product stream is then partially hydrogenated to produce aldehydes in a hydrogenation reactor (A). The aldehydes are then distilled off in a distiller or a distillation tower (C). The remaining ozonated product stream is then oxidized in an oxidation chamber (D) to generate acids. Excess oxygen (from D) and excess hydrogen (from A) are then fed into a fuel cell to generate electricity and/or water. Optionally, excess oxygen is recycled to the ozone reactor. A schematic of hybrid ozonolysis is shown in FIG. 2.

Example 3

Hybrid Ozonolysis of Fatty Acid Derived from Algae

Figure 3:
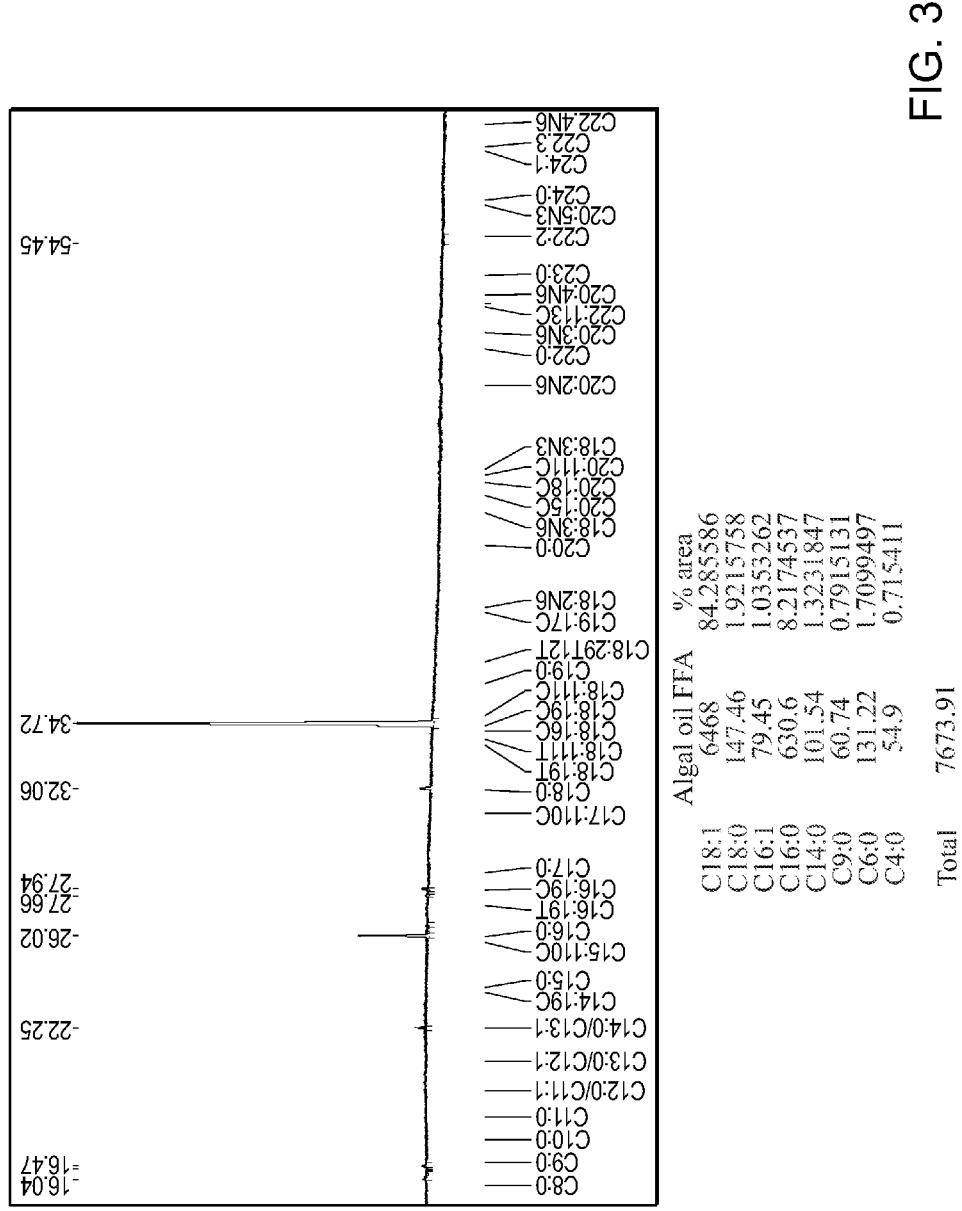
FIG. 3 shows a Flame Ionization Detector Gas Chromatography (GC FID) trace of the algal fatty acid methyl esters used for certain hybrid ozonolysis experiments. The included table shows the free fatty acid composition.

Fatty acid derived from algae was used as a starting material. The composition of this fatty acid was determined using the methyl ester derivatization technique described in AOAC Official Method 969.33 *Fatty Acids in Oils and Fats. Official Methods of Analysis of the AOAC*, 17th edn, AOAC, Arlington, Va. USA, (2000), followed by GC FID analysis, the results of which are shown in FIG. 3. According to peak integration, the starting fatty acid was determined to be about 84% oleic acid.

Ozonolysis 300 g of fatty acid derived from algae was combined with 300 g of water in a 2 liter batch reactor and stirred at 800 rpm with an initial temperature of 20° C. Ozone was then sparged through the mixture at a rate of 6.5 liters per minute and a concentration of 75 g/m$^3$ ozone for 100 minutes. The temperature rose during the reaction but did not exceed 50° C. After 100 minutes, the reaction mixture was purged of $O_2$ and $O_3$ by sparging with $N_2$.

Reduction

Figure 4:
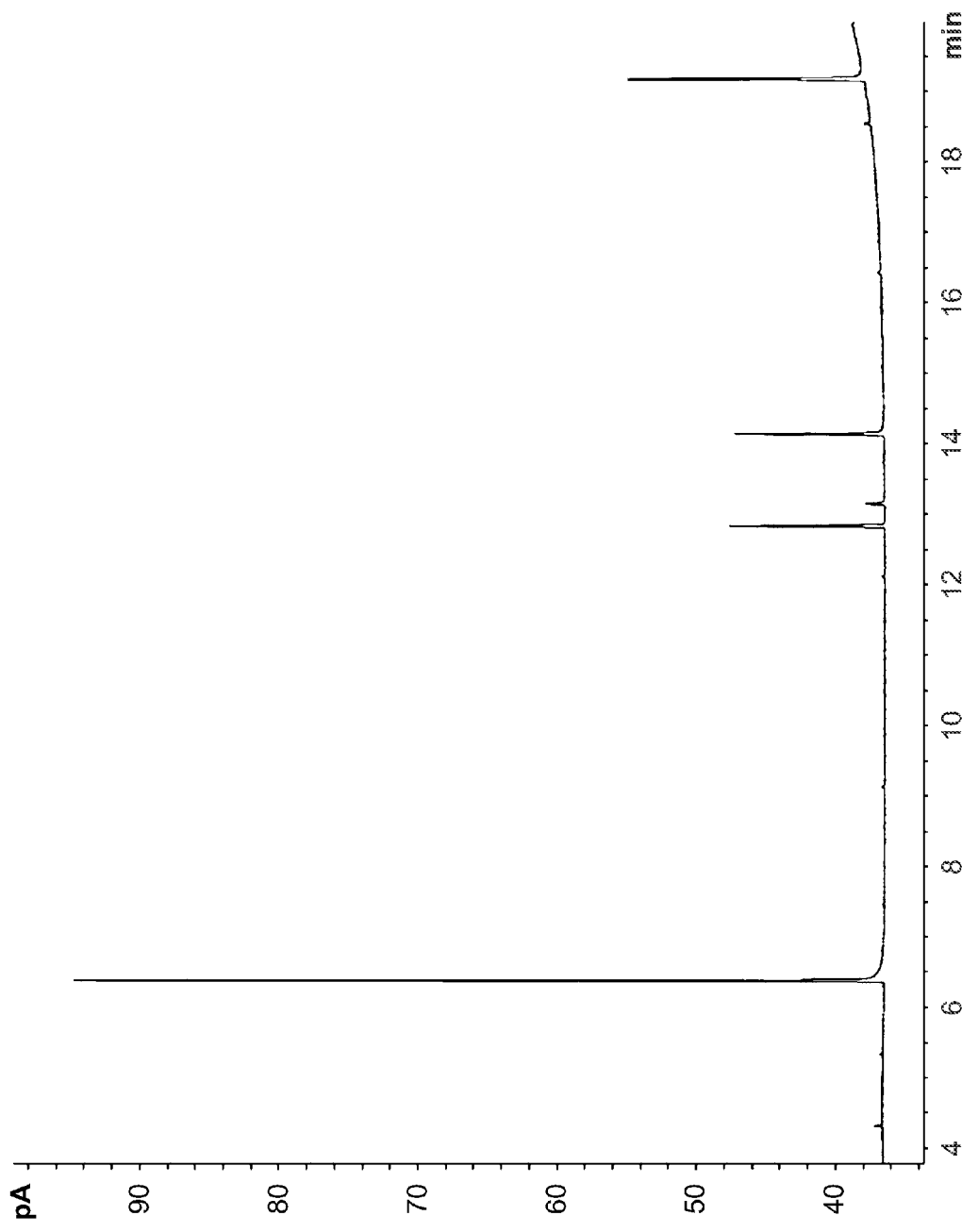
FIG. 4 shows a GC FID trace of the organic phase after reduction described in Example 3. Note that the nonanal peak is at ~6.4 minutes, the internal standard at ~12.8 minutes, and nonanoic acid at ~14.1 minutes.

The aqueous mixture of ozonated fatty acid derived from algae was then transferred to a high-pressure vessel and charged with 0.25% by wt. palladium black and placed under 350 psi $H_2$ at 70° C. The reaction mixture was vigorously stirred for 80 minutes and then the reaction was brought to ambient pressure and filtered to remove catalyst while the reaction mixture was still >40° C., or ~60° C. The organic and aqueous phases readily separated and the organic phase was partitioned off for ~280 g of organic material. Slightly less than theoretical was obtained largely due to transfer losses between vessels. A GC FID trace of this material can be seen in FIG. 4. Note that not all molecules are sufficiently volatile to be seen in this trace, specifically stearic acid, however, when used in conjunction with calibration curves it is estimated that the organic phase is ~25% nonanal and ~7.7% nonanoic acid.

Separation

Figure 5:
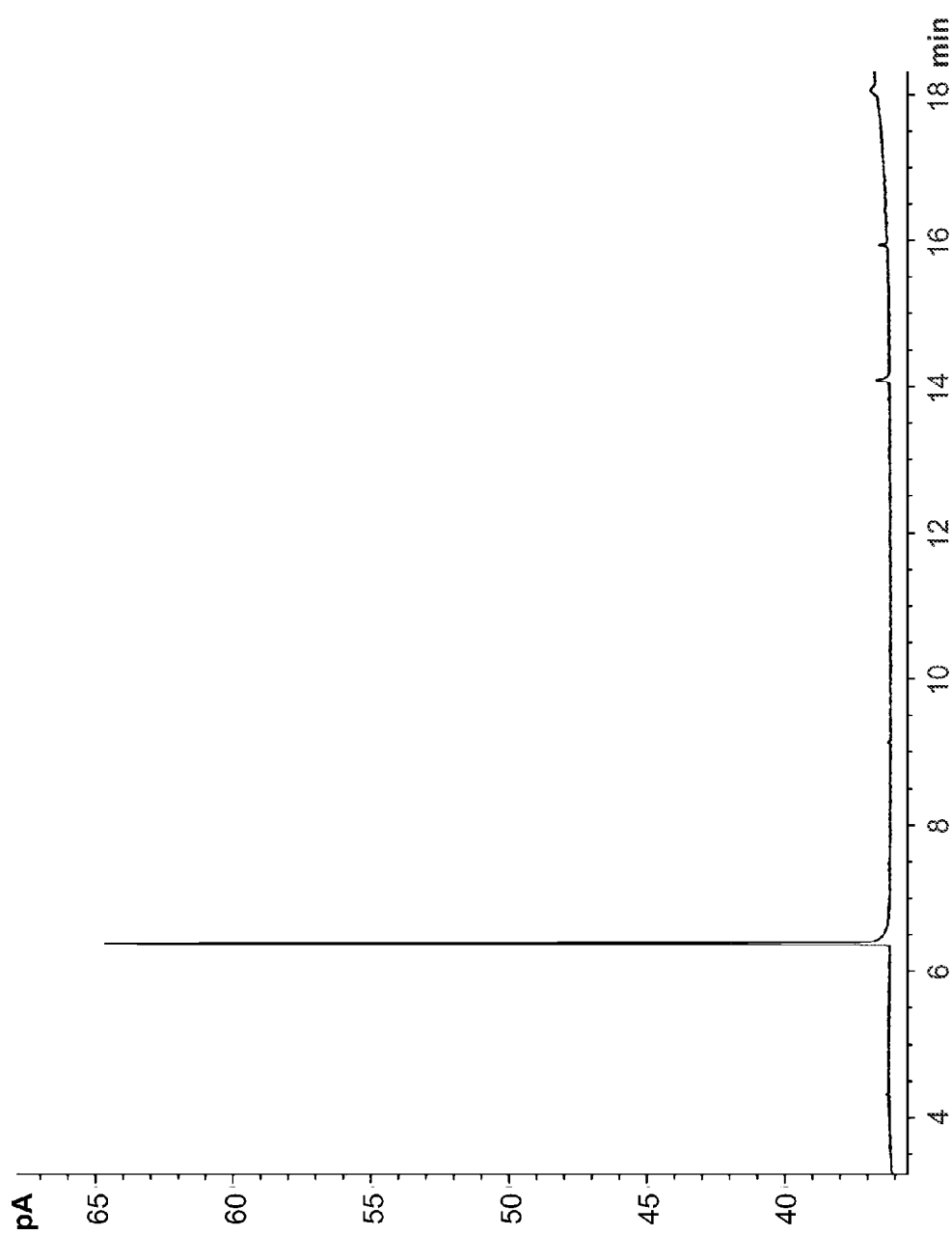
FIG. 5 shows a GC FID trace of the distillate collected from hybrid ozonolysis of algal fatty acid described in Example 3. Integration suggests >97% nonanal, represented by the peak at ~6.4 minutes.

A short path wiped film evaporator (Incon ICL-04) was then used to fractionate the organic material. The organic material (280 g) was added dropwise to the distillation chamber, which was kept at a reduced pressure of 0.8-1.0 mbar. The distillation surface was kept at 50° C. while the condenser temperature was kept at 0° C. and the cold trap was kept chilled with dry ice. Distillate (69 g) was recovered that was determined to be >97% nonanal by GC FID (FIG. 5). Heavy residue (190 g) was also collected that turned to a white solid upon cooling to room temperature. The balance of volatile material was collected in the dry ice trap.

Oxidation

Figure 6:
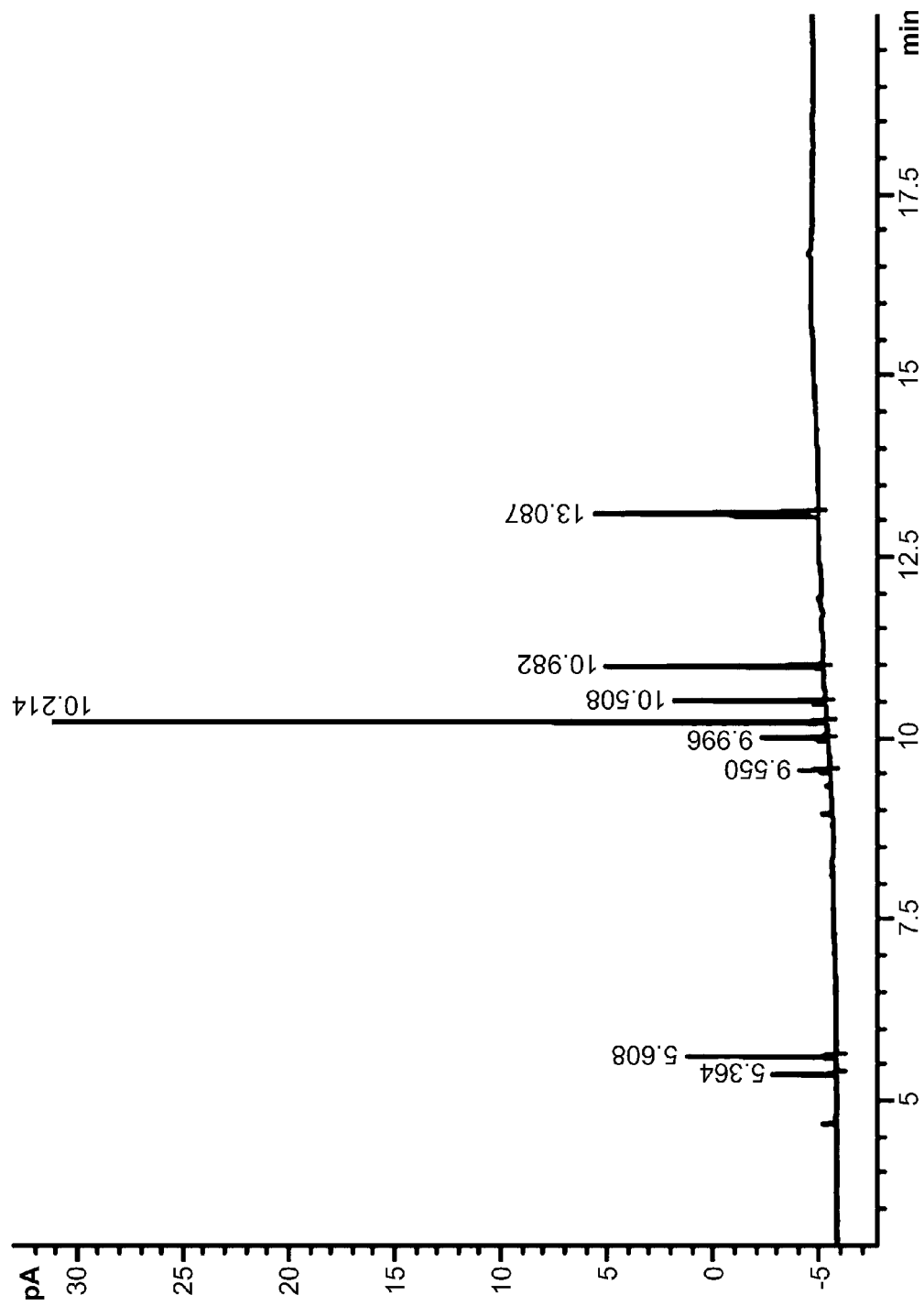
FIG. 6 shows a GC FID trace of the heavy residue recovered after distillation and methyl ester and dimethyl acetal derivatization described in Example 3. From left to right, nonanal dimethyl acetal (5.364 min), nonanoic methyl ester (5.608 min), azelaldehyde (i.e., 9-oxononanoic acid) methyl ester (9.996 min), azelaldehyde methyl ester dimethyl acetal (10.214 min), azelaic acid dimethyl ester (10.508 min), palmitic acid methyl ester (10.982 min), and stearic acid (13.087 min).

A portion of the white, heavy residue from separation was analyzed using a modification of the methyl ester derivatization technique described in AOAC Official Method 969.33 *Fatty Acids in Oils and Fats. Official Methods of Analysis of the AOAC*, 17th edn, AOAC, Arlington, Va. USA, (2000). The sole modification was the omission of alkaline, which would have degraded the aldehydic materials present in the sample. Using this modified method, the majority, but not all, of the aldehydes were converted to the corresponding dimethyl acetal. GC FID analysis of these methyl ester/acetal derivatives suggested that the material was ~42% azelaldehyde (i.e., 9-oxononanoic acid) and ~8% azelaic acid with much of the balance being nonanoic acid (~6.8%), palmitic acid (14%) and stearic acid (24.55%). This result can be seen in FIG. 6. Note that azelaldehyde is represented by peaks at 9.996 min (assigned as azelaldehyde methyl ester) and 10.214 min (assigned as azelaldehyde methyl ester dimethyl acetal).

Figure 7:
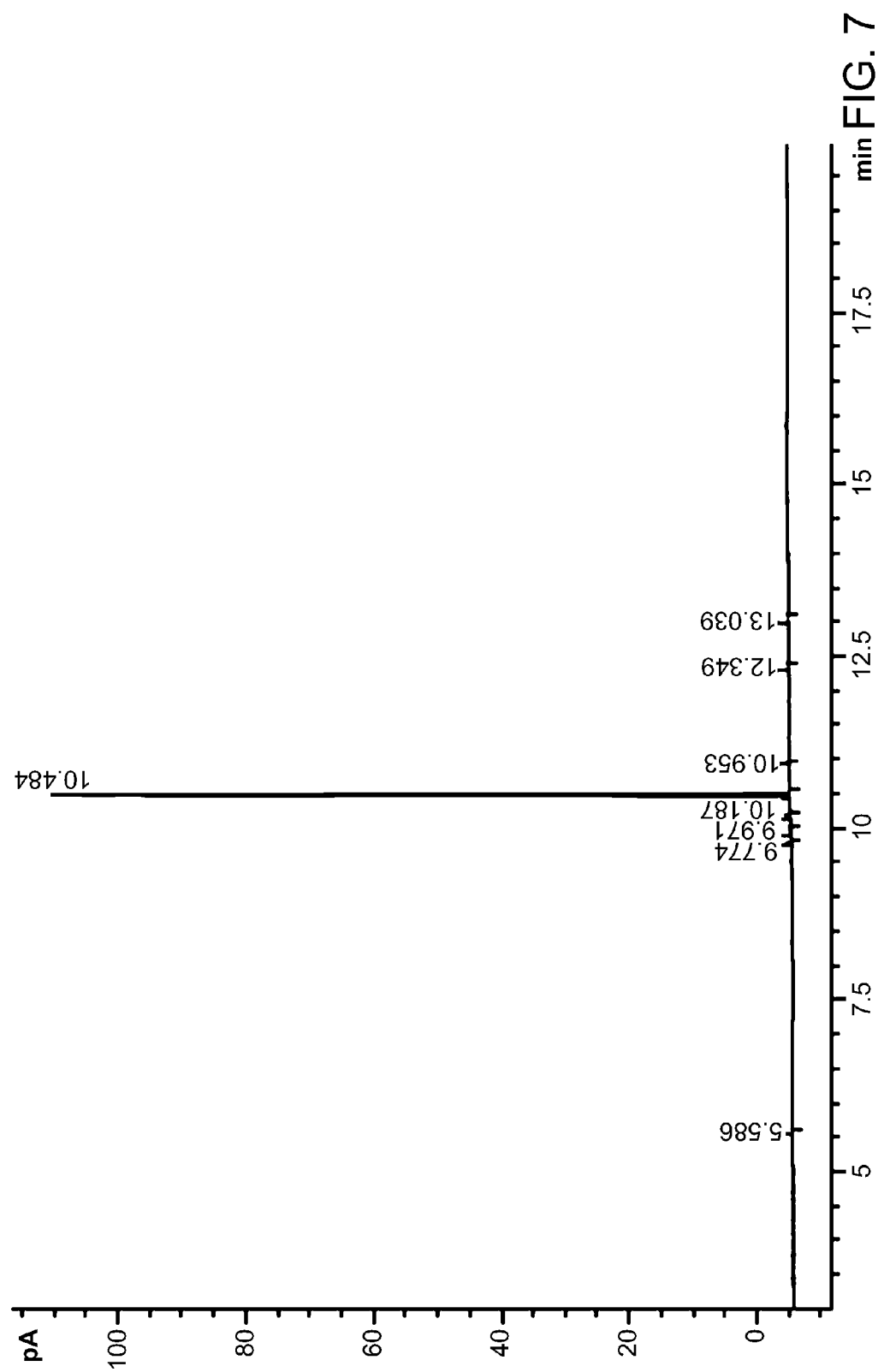
FIG. 7 shows a GC FID trace of azelaic acid obtained from the hybrid ozonolysis process after methyl ester derivatization. Integration suggests >97% azelaic acid.
Figure 8:
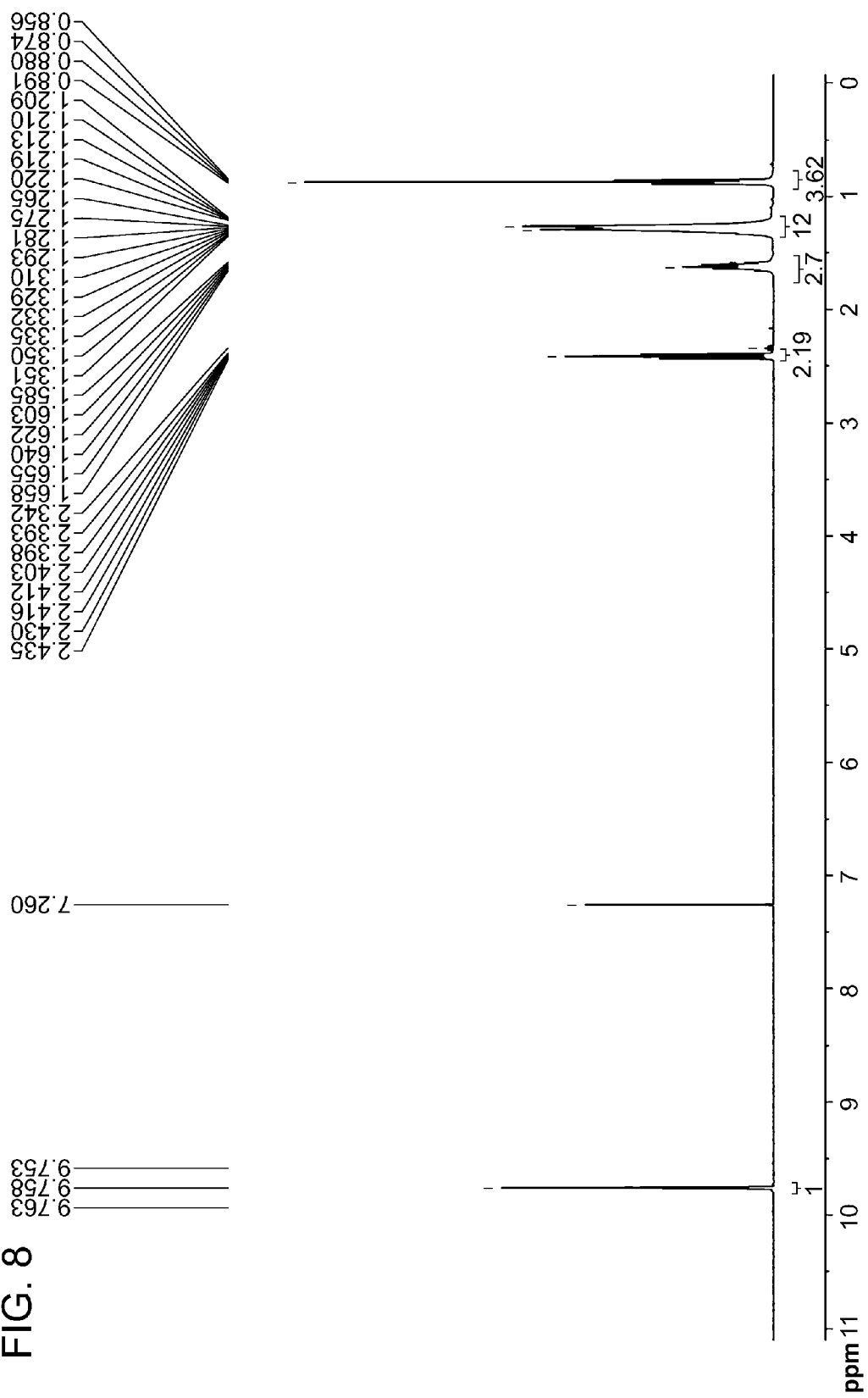
FIG. 8 shows a $^1$H NMR of the nonanal described in FIG. 5, with $CDCl_3$ used as solvent.
Figure 9:
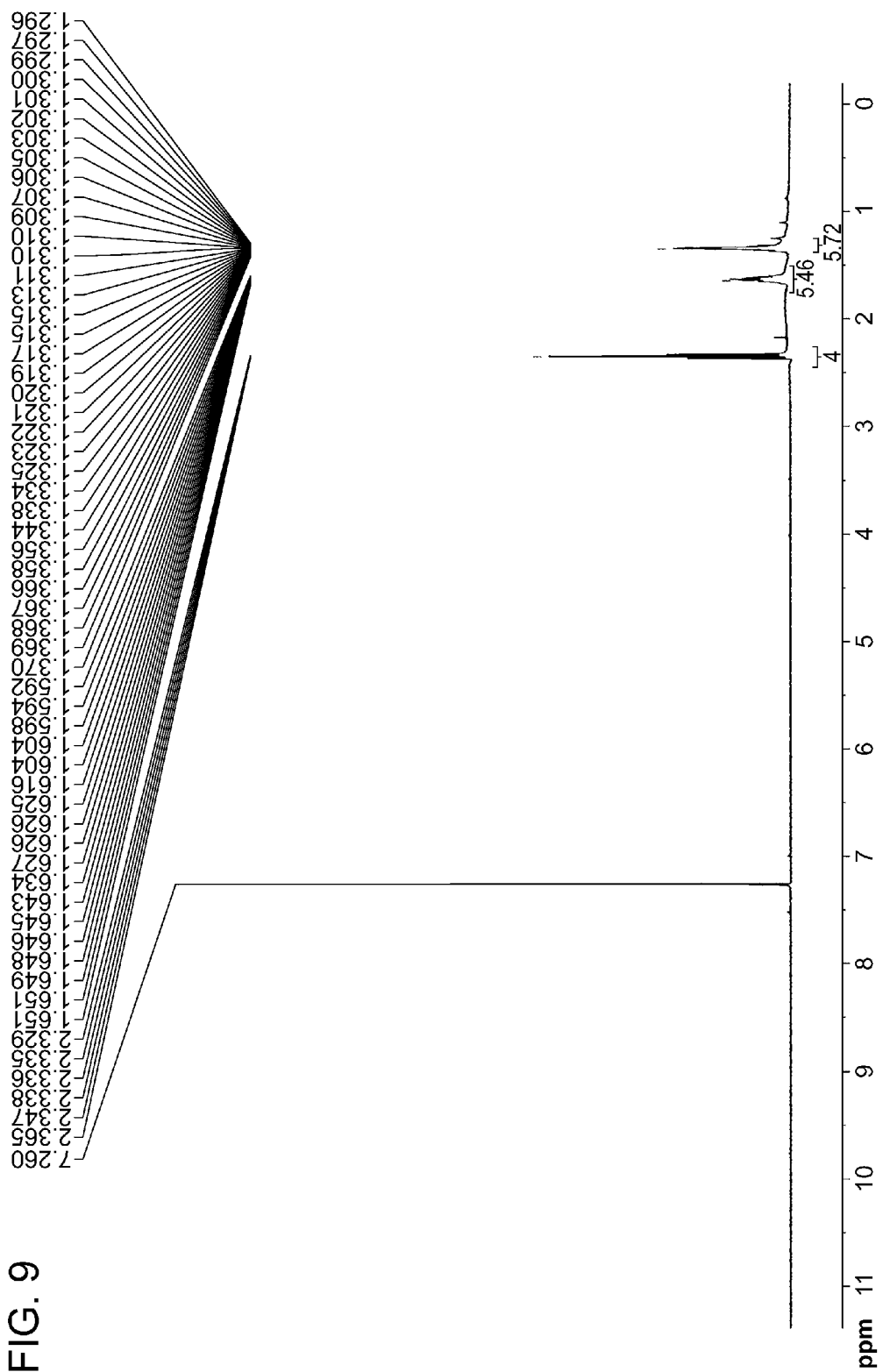
FIG. 9 shows $^1$H NMR of the azelaic acid described in FIG. 7, with $CDCl_3$ used as solvent.

61.2 g of the white, heavy residue from separation step was charged with 104.8 mg of $Mn(OAc)_2$ in a round bottom flask and was heated to 75° C. $O_2$ was then sparged through the mixture using a coarse frit for 3 hours. 100 ml of $H_2O$ was added to the mixture to remove all solids from the sidewall of the flask and sparging was continued for another 2 hours. The organic phase was then extracted with $H_2O$ at elevated temperature (>50° C. or ~70° C.) two times with 150 ml $H_2O$ and two times with 100 ml $H_2O$. The aqueous fractions were then extracted with heptane two times (100 ml heptane each) at elevated temperature. The aqueous phase was then allowed to cool to room temperature. Upon cooling white crystals formed in the aqueous layer, which were then collected with filtration. After drying under high vacuum, 18.5 g of white crystals were obtained. An analytical sample was then derivatized as the methyl ester using the aforementioned modification of AOAC Method 969.33 *Fatty Acids in Oils and Fats. Official Methods of Analysis of the AOAC*, 17th edn, AOAC, Arlington, Va. USA, (2000), and analyzed using GC FID, the results of which can be seen in FIG. 7. Integration suggested the material is >97% azelaic acid. Some azelaic acid still remained in the organic phase and could be recovered with additional hot aqueous extractions. The heptane extraction should be regarded as an optional step that results in a slightly improved purity of the recovered azelaic acid.

Example 4

Hybrid Ozonolysis of Methyl Canolate with Methyl 9-Oxononanoate Isolation

Methyl canolate (also known as canola oil fatty acid methyl ester) was prepared according known procedures for converting vegetable oils into fatty acid methyl esters. According to GC analysis the composition of this material is as follows: methyl oleate (57.36%), methyl palmitate (4.17%), methyl linoleate (20.27%), methyl linolenate (8.2%), and methyl stearate (1.83%).

Ozonolysis

Methyl Canolate (300 g) was combined with 600 g of $H_2O$ and was cooled to 20° C. while vigorously stirring. Ozone was introduced to the system at a flow rate of 7 L/min with a maximum concentration of 100 g/m$^3$ for a total of 110 minutes. GC FID indicated greater than 95% consumption of starting material. The reaction mixture was then purged with $N_2$ and was taken on as it was without further purification.

Reduction

The aqueous mixture of oxidized methyl canolate was combined with 0.25% Pd black (by wt. of methyl canolate), placed under 350 psi of $H_2$ pressure, and was heated to 75° C. until peroxide titration indicated the absence of peroxide. The mixture was then removed from heat and pressure and was filtered to recover Pd. The resulting mixture was biphasic and quickly phase separated in an extraction funnel. The top, organic phase (a light yellow liquid; 293 g) was partitioned off and carried on as it was. (Note: after extraction of the aqueous phase with ethyl acetate, another 5 g of organic material was recovered and was set aside).

Separation

A short path wiped film evaporation system (Pope Scientific 2" Wiped Film Still) was then used to fractionate the organic material. 293 g of liquid was loaded into the feeder and was fed dropwise down the column which was maintained at 1.0-1.1 mbar pressure with a 50° C. jacket temperature, a −10° C. condenser temperature, and a dry ice/acetone trap. 100.3 g of light aldehydic material was evaporated off consisting of mostly nonanal and hexanal. The resulting heavy residue (179 g) was again distilled on the wiped film evaporator under 0.2-0.3 mbar pressure with a 50° C. jacket temperature, a −10° C. condenser temperature, and a dry ice/acetone trap. 46 g of methyl 9-oxononanoate was isolated in the distillate at greater than 80% purity. This material can be taken on for oxidation as described in example 3 or can be taken on for other uses.

Example 5

Oxidation and Crystallization of an Acid—Ester, Monomethyl Brassylate

Following procedures similar to those described in previous examples, 500 g of methyl erucate (89% by GC FID) was ozonolyzed, reduced, and distilled to remove the majority of the light alkyl aldehydes (almost exclusively nonanal), resulting in 380 g of heavy residue containing largely nonanoic acid, 13-oxotridecanoate methyl ester, and monomethyl brassylate. This material was taken as was for oxidation and crystallization as described below.

Oxidation

Figure 10:
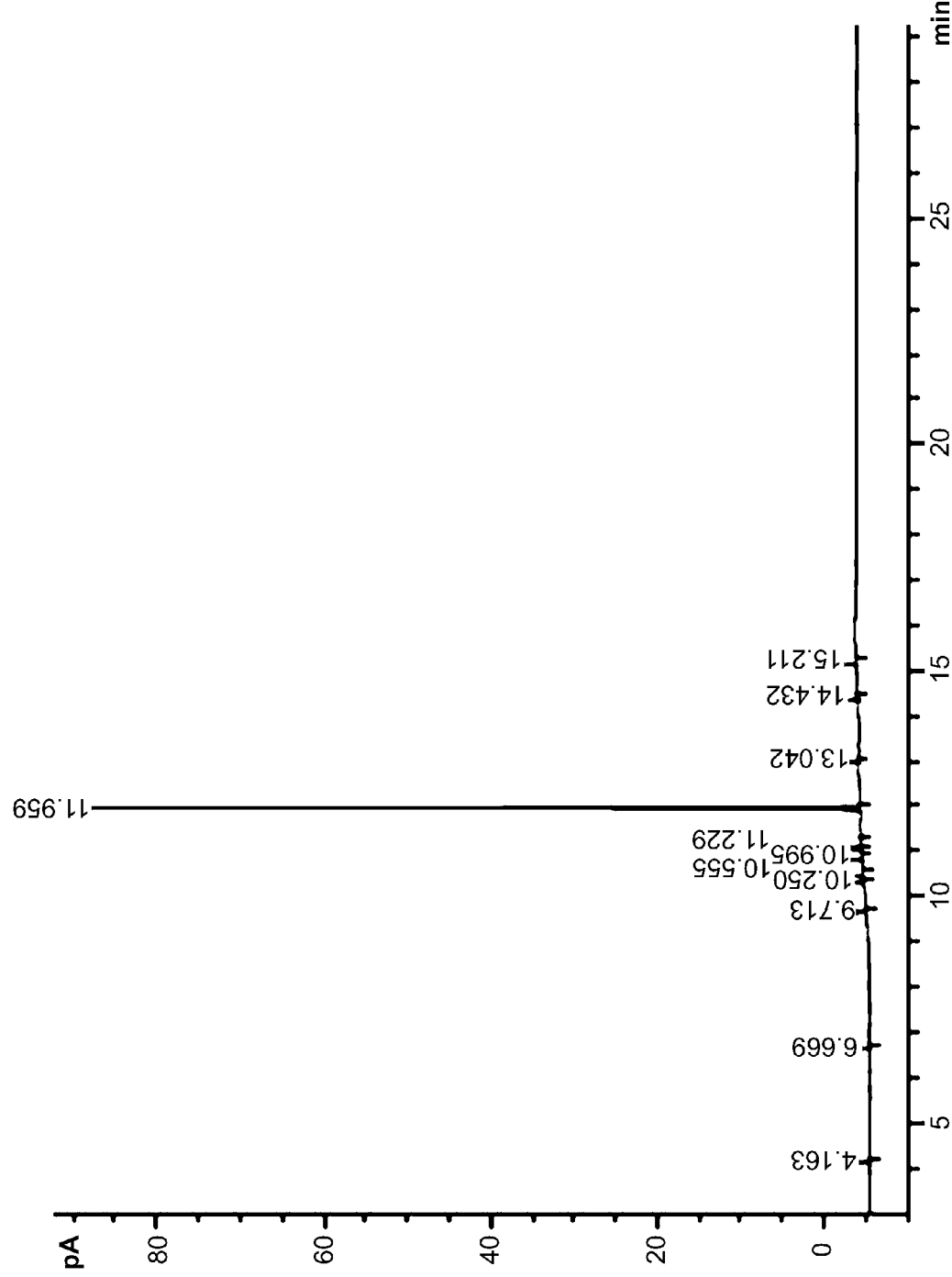
FIG. 10 shows GC FID trace of monomethyl brassylate after the hybrid ozonolysis process after methyl ester derivatization. Integration suggests 96.5% monomethyl brassylate.
Figure 11:
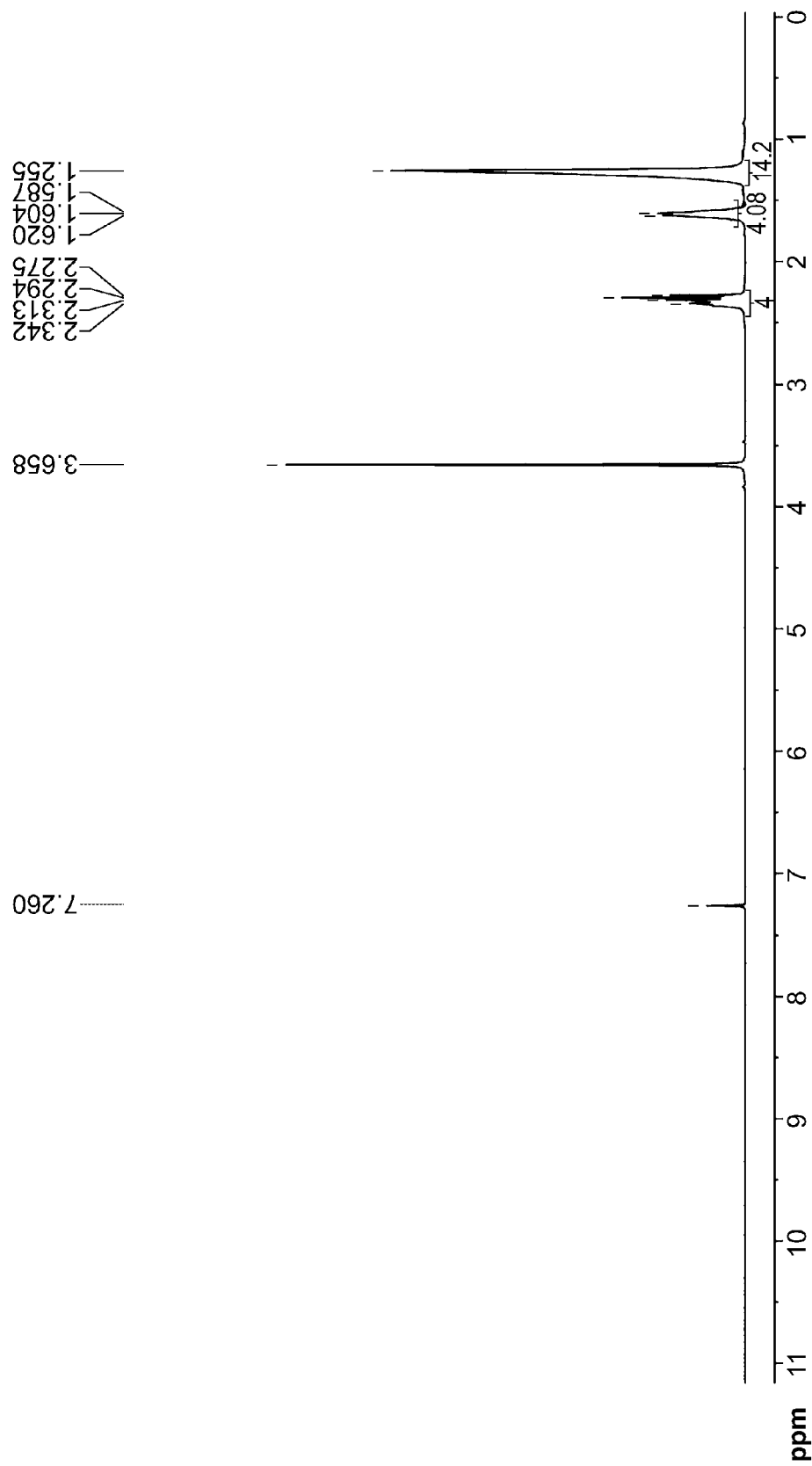
FIG. 11 shows $^1$H NMR of the monomethyl brassylate described in FIG. 10, with $CDCl_3$ used as solvent.

The heavy residue (380 g) was charged with 380 mg of Mn(OAc)$_2$ and was heated to 100° C. while sparging with O$_2$ and stirring. The solution turned a dark brown and was left to react for 160 minutes until GC indicated that all 13-oxotridecanoate methyl ester was converted to the corresponding acid, monomethyl brassylate. This material was then taken up in heptane (3× the weight of the substrate) and was heated to 90° C. Upon cooling crystals formed which were then filtered. These crystals were then again recrystallized from hot heptane, resulting in 60 g of monomethyl brassylate as a white crystalline solid. GC FID of this material is shown in FIG. 10, and the $^1$H NMR in FIG. 11. The balance of the material can be continuously crystallized in this fashion to isolate additional monomethyl brassylate.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method comprising:
    a) providing oxygen and hydrogen, wherein said oxygen treated with electricity to generate ozone; wherein said ozone is used in ozonolysis of a fatty acid or a fatty acid ester in an ozone reactor;
    b) inputting said fatty acid into said ozone reactor, in which said fatty acid or fatty acid ester absorbs said ozone, thereby forming a mixture comprising ozonated product stream comprising one or more compounds selected from ozonide, peroxide, aldehyde, ester, and acid; and
    c) generating partially reduced products comprising a linear alkyl aldehyde and oxygenated products comprising a diacid or acid-ester from said ozonated product stream by:
        i. partially reducing said ozonated product stream after said ozonated product stream enters a hydrogenation chamber to generate said partially reduced products comprising largely a linear alkyl aldehyde, and contacting said partially reduced products with water, forming two layers comprising an organic phase while leaving the hydrogenation chamber;
        j. fractionating said organic phase to separate said linear alkyl aldehyde from the remaining organic phase; and
        k. oxidizing the remaining organic phase after fractionation at step (j) after the remaining organic phase enters into an oxidation chamber, resulting in the generation of said oxygenated products comprising said diacid or acid-ester;
    thereby generating said linear alkyl aldehyde and said diacid or acid-ester from said ozonated product stream,
    wherein the linear aldehyde, oxo-acid, oxo-ester, acid-ester, or diacid is more than about 95% pure.

2. The method of claim 1, wherein the linear aldehyde, oxo-acid, oxo-ester, acid-ester, or diacid is more than about 99% pure.

* * * * *